United States Patent
Davis et al.

(10) Patent No.: US 10,039,879 B2
(45) Date of Patent: *Aug. 7, 2018

(54) INFUSION SYSTEM WITH DUAL-CHAMBERED RESERVOIR

(71) Applicant: CareFusion 303, Inc., San Diego, CA (US)

(72) Inventors: Lisa Davis, San Diego, CA (US); Robert Butterfield, San Diego, CA (US)

(73) Assignee: CareFusion 303, Inc., San Diego, CA (US)

(*) Notice: Subject to any disclaimer, the term of this patent is extended or adjusted under 35 U.S.C. 154(b) by 11 days.

This patent is subject to a terminal disclaimer.

(21) Appl. No.: 15/354,635

(22) Filed: Nov. 17, 2016

(65) Prior Publication Data

US 2017/0128666 A1    May 11, 2017

Related U.S. Application Data

(63) Continuation of application No. 13/841,369, filed on Mar. 15, 2013, now Pat. No. 9,498,574.

(51) Int. Cl.
*A61M 5/145* (2006.01)
*A61M 39/20* (2006.01)
(Continued)

(52) U.S. Cl.
CPC .... *A61M 5/14526* (2013.01); *A61M 5/14593* (2013.01); *A61M 5/31515* (2013.01);
(Continued)

(58) Field of Classification Search
CPC .......... A61M 5/14526; A61M 5/14586; A61M 5/14593; A61M 5/31515
See application file for complete search history.

(56) References Cited

U.S. PATENT DOCUMENTS 5,135,491 A    8/1992  Baldwin
5,261,235 A    11/1993 Shellhause
(Continued)

FOREIGN PATENT DOCUMENTS

CN    101257939 A    9/2008
JP    H8336573 A    12/1996
(Continued)

*Primary Examiner* — Nathan R Price
*Assistant Examiner* — Melissa A Snyder
(74) *Attorney, Agent, or Firm* — Mintz Levin Cohn Ferris Glovksy and Popeo, P.C.

(57) ABSTRACT

Described herein are medical fluid infusion systems for pumping a fluid to a patient, such as in a hospital environment. In one aspect, disclosed is an infusion system including a drive assembly having a drive fluid reservoir and a drive mechanism configured to apply a force to drive fluid from the drive fluid reservoir through a length of tubing. The infusion system includes a hydraulic assembly having a first fluid chamber having an inlet port configured to be in fluid communication with the length of tubing and a second fluid chamber having an outlet port configured to be in fluid communication with a patient extension set and a flexible movable divider sealing the first fluid chamber from the second fluid chamber. Related apparatus, systems, techniques and articles are also described.

25 Claims, 8 Drawing Sheets

(51) Int. Cl.
*A61M 5/315* (2006.01)
*A61M 5/14* (2006.01)

(52) U.S. Cl.
CPC ..... *A61M 39/20* (2013.01); *A61M 2005/1402* (2013.01); *A61M 2039/205* (2013.01); *A61M 2205/3331* (2013.01); *A61M 2205/583* (2013.01); *A61M 2205/7536* (2013.01)

(56) References Cited

U.S. PATENT DOCUMENTS

| | | | |
|---|---|---|---|
| 5,306,257 A | 4/1994 | Zdeb | |
| 6,063,058 A | 5/2000 | Sakamoto | |
| 7,356,382 B2 | 4/2008 | Vanderveen | |
| 9,089,636 B2 | 7/2015 | Gonnelli | |
| 2005/0070915 A1* | 3/2005 | Mazzuca | A61B 17/8822 606/93 |
| 2006/0069382 A1 | 3/2006 | Pedersen | |
| 2008/0243129 A1* | 10/2008 | Steffen | A61B 17/8822 606/93 |
| 2011/0087186 A1 | 4/2011 | Kirchhofer | |
| 2012/0136256 A1* | 5/2012 | Nozaki | A61B 8/4263 600/459 |

FOREIGN PATENT DOCUMENTS

| | | |
|---|---|---|
| JP | H11137681 A | 5/1999 |
| JP | 200042088 A | 2/2000 |
| WO | WO-93/21987 A1 | 11/1993 |
| WO | WO-2004/089448 A1 | 10/2004 |

* cited by examiner

INFUSION SYSTEM WITH DUAL-CHAMBERED RESERVOIR

CROSS REFERENCE TO RELATED APPLICATION

This application is a continuation of U.S. patent application Ser. No. 13/841,369, titled "INFUSION SYSTEM WITH DUAL-CHAMBERED RESERVOIR," filed Mar. 15, 2013, the disclosure of which is hereby incorporated by reference in its entirety herein.

BACKGROUND

Intravenous (IV) fluid delivery pumps are used to deliver fluid to a patient or to draw out fluid from a patient's body. IV fluid infusion typically requires patients to be tethered to the pump by the IV line. This can limit patient mobility and cause a significant amount of medical fluid to be lost in the dead space of the IV line. Further, a long IV line can increase the amount of time before a patient receives the medication. In order to increase the patient's mobility, the patient can be disconnected from the IV line or the length of the IV line may be increased. However, disconnecting the IV line from the patient increases the chance of blood stream infections, result in line obstructions and excessive false alarms. Increasing tubing lengths also adds to dead space in the line.

Further, the tubing is generally formed of flexible materials such as polyvinyl chloride (PVC), polyurethane and silicone rubber. The tubing and plastic components of the system can be affected or degraded by exposure to certain therapeutic agents that damage the plastic and/or causing the release of chemicals into the fluid path. Silicone rubber has a relatively high permeability rate of oxygen and nitrogen transfer thereby presenting a risk of gas migration from the atmosphere through the tubing wall and into the medical fluid. This gas transfer may lead to gas bubbles within the medical fluid, which, if transported through the tube and into the bloodstream of a patient, present a hazard to the patient for air embolism. PVC provides a good gas barrier but can contain di-ethylhexyl phthalate (DEHP) plasticizer that tends to leach out into the medical fluid, in particular oncology medications such as docetaxel and paclitaxel.

In view of the foregoing, there is a need for improved fluid delivery systems.

SUMMARY

Described herein are medical fluid infusion systems for pumping a fluid to a patient, such as in a hospital environment.

In one aspect, disclosed is an infusion system including a drive assembly having a drive fluid reservoir and a drive mechanism configured to apply a force to drive fluid from the drive fluid reservoir through a length of tubing. The infusion system includes a hydraulic assembly having a first fluid chamber having an inlet port configured to be in fluid communication with the length of tubing and a second fluid chamber having an outlet port configured to be in fluid communication with a patient extension set and a flexible movable divider sealing the first fluid chamber from the second fluid chamber.

The force applied by the drive mechanism can propel the fluid from the drive fluid reservoir through the length of tubing into the first fluid chamber to move the divider causing infusate to exit the second fluid chamber through the outlet port. The divider can be slidingly positioned between the first fluid chamber located on a proximal side of the divider from the second fluid chamber located on a distal side of the divider. Fluid propelled into the first fluid chamber can move the divider in a distal direction to deliver infusate contained in the second fluid chamber through the outlet port. The hydraulic assembly can be a syringe assembly having a syringe barrel and the divider is positioned within the syringe barrel. The system can further include a plunger reversibly coupled to the divider and having a detachable handle.

The system can further include a cap coupled to and sealing off a proximal end of the first fluid chamber. The cap can have a stem portion configured to extend within and seal with an inner surface of the first fluid chamber. The inlet port can extend through the cap. The cap can further include a vent filter. The drive assembly can further include one or more pressure sensors. The drive assembly can further include one or more visual indicators providing information regarding operation of the system. The one or more visual indicators can include one or more LEDs illuminating one or more components of the system. A color of the one or more LEDs can indicate infusion status. The length of tubing can be low-compliance tubing. The hydraulic assembly can be reversibly coupled to the drive assembly. The patient extension set can be less than at least about 6 inches. The patient extension set can have a priming volume of less than about 0.7 mL.

The hydraulic assembly can further include a bag formed by a first flexible layer, a second flexible layer and a third flexible layer. Perimeter sealing of the first and second flexible layers can form the first fluid chamber. Perimeter sealing of the second and third flexible layers can form the second fluid chamber. The second flexible layer can be the flexible movable divider. The hydraulic assembly can further include a rigid, fixed volume housing inside which the bag is enclosed. The housing can maintain a constant volume to the bag.

The details of one or more variations of the subject matter described herein are set forth in the accompanying drawings and the description below. Other features and advantages of the subject matter described herein will be apparent from the description and drawings, and from the claims.

DETAILED DESCRIPTION

Described herein are medical fluid infusion systems for pumping a fluid to a patient, such as in a hospital environment. More particularly, described herein are drug infusion systems incorporating dual-chambered reservoirs for delivering medical fluid infusate to a patient in a closed configuration isolating the infusate from the pumping assembly components. The infusion systems described herein provide the advantage of low priming volumes and short extension sets for delivering fluid from the system to a patient minimizing dead space in the line as the medication can be moved much closer to the patient. The infusion systems described herein can aid in the delivery of small volume fluids or fluids undergoing low flow rates or intermittent infusion. Other implementations of the infusion systems described herein can be used for larger volume fluid delivery. The infusion systems described herein can benefit patients desiring improved mobility during or in between infusions. The infusion systems described herein also can benefit patients, such as pediatric or neonatal patients, where low priming volumes are critical. Further, the infusion systems described herein can allow for improved delivery of costly or precious medical fluids such as bone marrow, stem cells or other materials, due to the decreased dead space in priming.

The infusion systems described herein can be used with existing infusion pumps such as the ALARIS System (CareFusion, San Diego, Calif.) or infusion pumps described in U.S. Pat. No. 7,356,382, which is incorporated by reference herein. It should also be appreciated that the described infusion systems are not limited to intravenous infusions, but can be used for any number of infusion types to a patient through a catheter including but not limited to parenteral, intraarterial, intracardiac, intraosseous, intramuscular, intrathecal, intraperitoneal, epidural, intracerebral, gastrointestinal, and the like.

Figure 1:
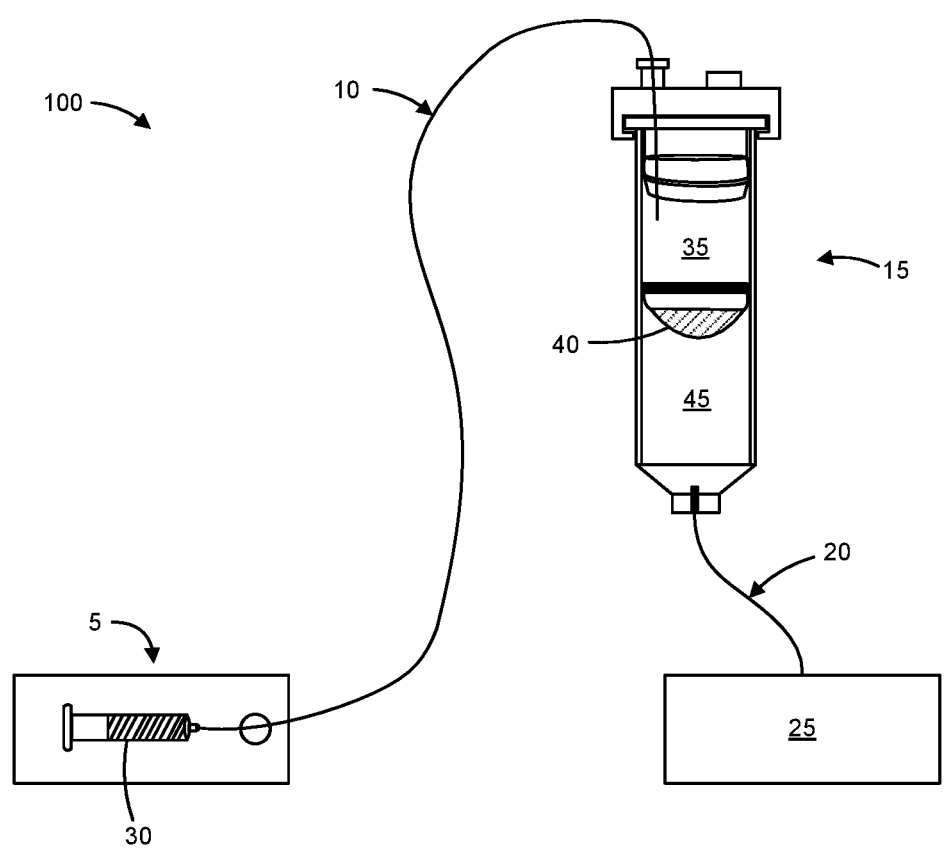
FIG. 1 is a schematic view of an infusion system according to one implementation.

FIG. 1 is a schematic view illustrating an infusion system 100 according to one implementation and incorporates a dual-chambered reservoir. The infusion system 100 can be a disposable system, but can also be reusable or incorporate reusable components. This implementation is particularly useful for small volume delivery although it should be appreciated that larger volumes can be delivered using the infusion system 100.

The infusion system 100 can include a drive assembly 5, tubing 10, a hydraulic assembly 15, and an extension set 20 extending from a distal end of the hydraulic assembly 15 to an access site on a patient 25. The hydraulic assembly 15 can include a dual-chambered syringe barrel wherein a first fluid chamber is in fluid communication with the tubing 10 and the drive assembly 5, and a second fluid chamber is in fluid communication with the extension set 20 and the patient access site 25. The first fluid chamber can be a drive chamber 35 located on a proximal side of a divider 40 located in the hydraulic assembly 15. The second fluid chamber can be an infusate chamber 45 located on a distal side of the divider 40. As will be described in more detail herein, the drive chamber 35 can receive drive fluid, such as water or another fluid type, propelled by the drive assembly 5 through tubing 10. Drive fluid driven into the drive chamber 35 can urge the divider 40 in a distal direction causing infusate contained within an infusate chamber 45 to be delivered out through the extension set 20 towards the access site of the patient 25.

Again with respect to FIG. 1, the drive assembly 5 can include a drive fluid reservoir 30 and a motor or pumping element (not shown) that causes the flow of fluid from the drive fluid reservoir 30 through an outlet into tubing 10. Tubing 10 can be low-compliance tubing. In some implementations, the drive fluid reservoir 30 can be a syringe barrel through which a plunger slides to expel sterile fluid from a distal outlet of the syringe barrel. It should be appreciated that the pump configuration of the drive assembly 5 can vary and need not be limited to a syringe pump configuration. The drive assembly 5 of the infusion system 100 can be configured to couple to or incorporate one or more components including inputs and control features, outputs such as a display or other features capable of providing alerts, programming and memory systems, communications systems, and other components of pumping assemblies.

The drive assembly 5 can be configured to drive fluid contained in the drive fluid reservoir 30 in a first direction through tubing 10 to flow into the drive chamber 35 of the hydraulic assembly 15. In some implementations, the drive assembly 5 causes the flow of fluid, preferably a sterile fluid, through the tubing 10 and into the drive chamber 35. The drive assembly 5 can also be configured to draw fluid in a reverse direction through tubing 10 to flow away from the hydraulic assembly 15, for example to refill the infusate chamber 45 with infusate as will be described in more detail below. The drive assembly 5 can include pressure sensing features to detect the pressure exerted by the pumping element or a change in pressure that may occur during an infusion, such as due to an occlusion. A pressure sensor can be disposed within the drive fluid side of the infusion system as well as in the infusate side of the infusion system or both.

The drive assembly 5 can incorporate visual indicators providing information to a user regarding operation of the infusion system 100. In some implementations, the drive assembly 5 can incorporate a visual indicator such as one or more LED lights transmitting light onto one or more parts of the drive assembly 5 such as the drive fluid reservoir 30. For example, one or more parts of the drive fluid reservoir 30 can be clear or translucent such that during operation, the light of the visual indicator can be transmitted through one or more regions of the drive fluid reservoir 30 and/or tubing 10. For example, as drive fluid is driven into tubing 10 and infusate is delivered to the patient, a green light (or some other color) can be transmitted such that tubing 10 appears green (or some other color) indicating active infusion status of the infusion system 100. When the infusion has ended, a red light (or some other color) can be transmitted such that tubing 10 appears red indicative of the end of the infusion. When the drive assembly 5 initiates refilling of the hydraulic assembly 15 with infusate, a blue light (or some other color) can be transmitted such that tubing 10 appears blue (or some other color) indicating refill status of the infusion system 100. It should be appreciated that one or more of regions of the infusion system 100 can be illuminated with one or more visual indicators.

Figure 2:
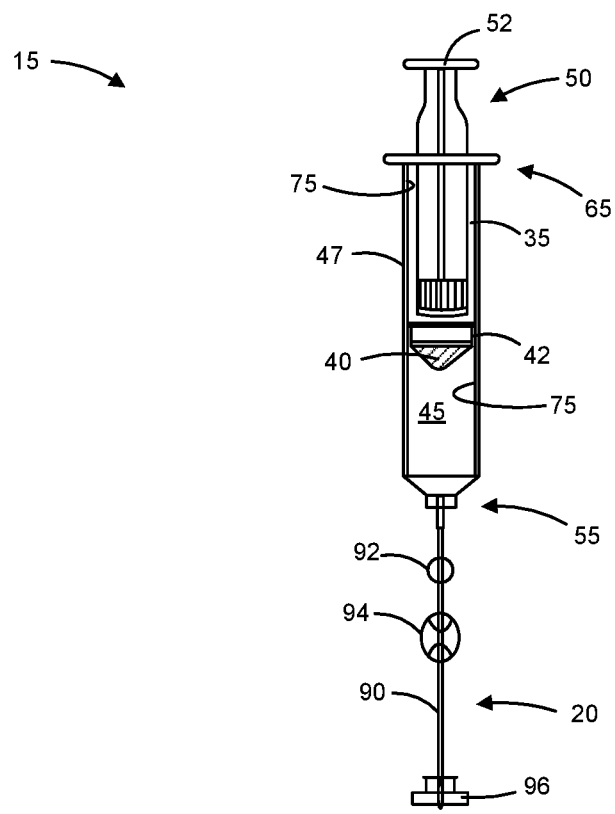
FIG. 2 is a schematic view of a hydraulic assembly coupled to an extension set according to one implementation.

FIG. 2 shows a schematic representation of the hydraulic assembly 15 coupled to an extension set 20. The hydraulic assembly 15 can include a divider 40, such as a stopper or a rigid plunger having a sealing surface such as an o-ring or quad-ring, located within a housing 47, such as a syringe barrel. The hydraulic assembly can be disposable following use. The divider 40 and housing 47 can be complementary in shape and slidably engaged with one another such that the divider 40 forms a slidable seal within the housing 47. The divider 40 can seal the proximal, drive chamber 35 from the distal, infusate chamber 45 forming a dual-chambered housing 47. The hydraulic assembly 15 can further include a plunger 50 having a detachable handle 52 that can extend through the drive chamber 35 to reversibly couple with the divider 40. The housing 47 can be formed of a suitable material, such as suitable polymeric, ceramic, metal, glass or other substantially rigid or hard material. In some embodiments, a sealing surface of the divider 40 or the divider itself can include a softer material than the housing 47, including a variety of elastomeric materials, such as, but not limited to, butyl rubber, silicon, liquid silicone rubber, synthetic rubber materials, fluoropolymer elastomers, and other medical grade materials. The divider 40 can include a plunger tip type sealing surface, as well as one or more O-rings or quad-rings coupled to one or more rigid components of the divider 40. The housing 47 can be any of a variety of sizes including 0.25 mL, 0.5 mL, 1 mL, 3 mL, 5 mL, 10 mL, 30 mL or higher. This implementation of the infusion system 100 is particularly useful for small volume delivery although it should be appreciated that larger volumes can be delivered using the infusion system 100.

Still with respect to FIG. 2, the housing 47 can define a bore or inner surface 75. The divider 40 can have an outer surface 42 for slidably engaging and sealing with the inner surface 75 of the housing 47. As mentioned previously, the divider 40 creates within the housing 47 two fluid chambers that are sealed from one another. One fluid chamber is the infusate chamber 45 located on the distal side of the divider 40 and configured to be in fluid communication with the distal outlet 55. The second fluid chamber is the drive chamber 35 located on the proximal side of the divider 40 and configured to be in fluid communication with the tubing 10.

The hydraulic assembly 15 can further include a distal outlet 55 configured to be coupled with the extension set 20. As shown in FIG. 2, the extension set 20 can include tubing 90 extending from the distal outlet 55 to the patient access site 25. The extension set 20 can include one or more of a clamp 92 such as a Halkey-Roberts or slide clamp, a stopcock 94 having a one-way valve, and a proximal, female connector and a distal male connector 96, such as a luer lock connector. The extension set 20 between the infusate chamber 45 and the access site 25 can remain undisturbed and its integrity maintained even when a patient is disconnected from the drive assembly 5. The hydraulic assembly 15 and/or the extension set 20 can be banded to a patient's arm or clipped to the patient's clothing during such periods of mobility.

The tubing 90 of the extension set 20 can be relatively short in length allowing for the hydraulic assembly 15 to be positioned near to the patient access site 25. The tubing 90 can be smallbore and microbore size having low priming volumes that vary depending on the tubing size and length. In some implementations, the tubing 90 can be at least about 1, 2, 3, 4, 5, 6, 8, or 10 inches in length. In some implementations, the tubing 90 can be less than at least about 6 inches. In some implementations, the tubing 90 is shorter than tubing 10. In some implementations, the priming volume is about 0.1 mL, 0.15 mL, 0.2 mL, 0.25 mL, 0.3 mL, 0.4 mL, 0.5 mL, 0.6 mL, 0.7 mL, 0.8 mL, 0.9 mL, or 1.0 mL. In some implementations, the priming volume is less than at least about 0.7 mL. In some implementations, the priming volume is approximately 0.2 mL. The extension set 20 is particularly useful for the treatment of pediatric or neonatal patients, as well as for the delivery of very small volumes, such as 1 cc, due to minimal dead space. This is advantageous for the delivery of bone marrow transplant material, stem cells or other costly or precious medical fluids. In some implementations, the extension set 20 is a SMARTSITE Extension Set (CareFusion, San Diego, Calif.).

Figure 3:
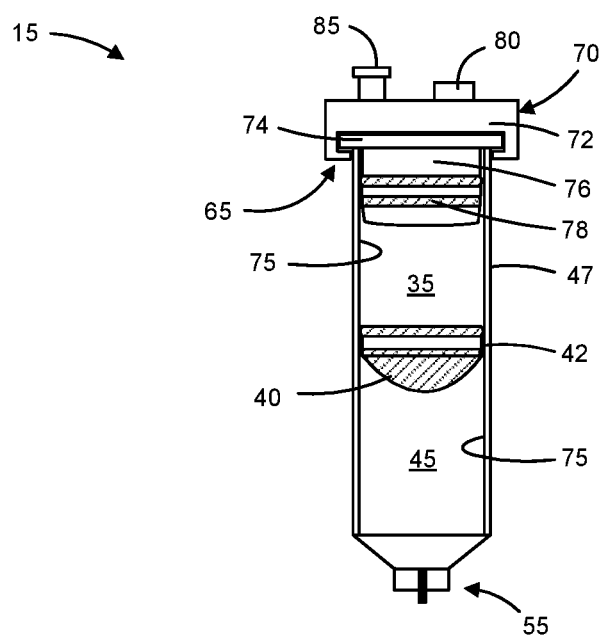
FIG. 3 is a schematic view of the hydraulic assembly of FIG. 1.

As shown in FIG. 3, the hydraulic assembly 15 can further include a proximal end 65 configured to be coupled to and locked with a cap 70. In some implementations, the cap 70 can include an upper portion 72 configured to mate with a mating feature 74 such as a thread or flange on the outer surface of the proximal end 65 of the housing 47. A lower, stem portion 76 of the cap 70 can extend within the housing 47 when the cap 70 is coupled to the proximal end 65. The stem portion 76 can include one or more seals 78, such as o-rings or quad-rings, configured to seal with the inner surface 75 of the housing 47. The upper portion 72 of the cap 70 can include a vent filter 80 as well as an access port 85 extending through the upper portion 72 and the stem portion 76 of the cap 70. In some implementations, the cap 70 can include a channel that vents air until the cap 70 is twisted into place closing off the vent. In some implementations, the vent filter 80 can visually identify to a user that the drive fluid reservoir is primed, for example by a color change. In some implementations, the access port 85 can be a SMARTSITE (CareFusion, San Diego, Calif.). The access port 85 can be configured to connect with tubing 10. The access port 85 can be configured to allow tubing to be reversibly connected and disconnected. In other implementations, the tubing is bonded to the access port 85 such that it is not reversibly connected. When the cap 70 is locked onto the proximal end 65 of the housing 47 and tubing 10 is connected with the access port 85, the drive chamber 35 and drive assembly 5 are in fluid communication. Drive fluid from the drive fluid reservoir 30 can be propelled through tubing 10 through the access port 85 and into the drive chamber 35. As fluid pressure increased within the drive chamber 35, the divider 40 can be urged distally such that the size of the infusate chamber 45 decreases and infusate within the infusate chamber 45 is expelled through the distal end 55 into the extension set 20.

Figure 4:
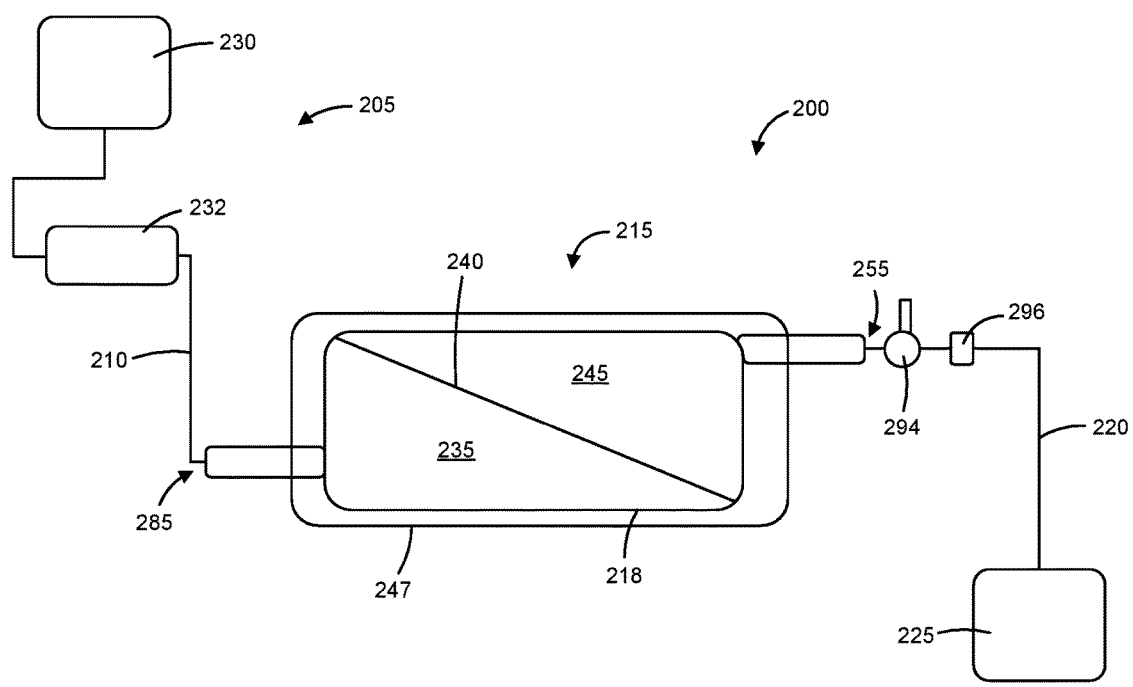
FIG. 4 is a schematic view of an infusion system according to another implementation.

FIG. 4 is a schematic view illustrating another implementation of an infusion system 200 also incorporating a dual-chambered reservoir that isolates the infusate side of the system from the pumping side of the system. This infusion system 200 can be a re-usable system, but can also be disposable or incorporate disposable components. This implementation can be used for large or small volume delivery.

The infusion system 200 can include a drive assembly 205, tubing 210, a hydraulic assembly 215, and an extension set 220 extending from an outlet 255 of the hydraulic assembly 215 to an access site on a patient 225. The hydraulic assembly 215 can have a dual-chambered reservoir 218 wherein a first fluid chamber is in fluid communication with the tubing 210 and the drive assembly 205, and a second fluid chamber is in fluid communication with the extension set 220 and the patient access site 225. The first fluid chamber can be a drive chamber 235 located on the "drive side" of a flexible divider 240 of the hydraulic assembly 215. The second fluid chamber can be an infusate chamber 245 located on an "infusate side" of the flexible divider 240. As will be described in more detail below, the drive chamber 235 can receive drive fluid that may or may not be sterile including water, saline, oil or another appropriate fluid type, propelled by the drive assembly 205 through tubing 210. The fluid need not be sterile as the drive fluid compartments are fully separated from the medication delivery compartment. Drive fluid driven into the drive chamber 235 can move the flexible divider 240 in a direction that causes infusate contained within the infusate chamber 245 to be delivered out through the extension set 220 towards the access site of the patient 225.

Again with respect to FIG. 4, the drive assembly 205 can include a drive fluid reservoir 230 and a pumping element 232 that causes the flow of fluid from the drive fluid reservoir 230 into tubing 210. In some implementations, the drive fluid reservoir 230 can be an IV bag hung from a pole or a syringe barrel type reservoir through which a plunger slides to expel the fluid from a distal outlet of the syringe barrel. It should be appreciated that the configuration of the drive assembly 205, including the drive fluid reservoir 230 and pumping element 232 can vary. The pump configuration can be a syringe pump or another pump type that is more suitable for larger volume pumping, such as a peristaltic type pump element. The drive assembly 205 of the infusion system 200 can be configured to couple to or incorporate one or more components including inputs and control features, outputs such as a display or other features capable of providing alerts, programming and memory systems, communications systems, and other components of pumping assemblies.

The pumping element 232 can be configured to drive fluid contained in the drive fluid reservoir 230 in a first direction through tubing 210 to flow into the drive chamber 235 of the hydraulic assembly 215. The pumping element 232 can also be configured to draw fluid in a reverse direction through tubing 210 to flow away from the hydraulic assembly 215, for example to refill the infusate chamber 245 with infusate. One or more components of the drive assembly 205, drive fluid reservoir 230 and pumping element 232 can include pressure sensing features to detect the pressure exerted by the pumping element 232 of a change in pressure that may occur during an infusion, such as due to an occlusion. A pressure sensor can be disposed within the drive fluid side of the infusion system as well as in the infusate side of the infusion system or both. The infusion system 200 can also incorporate visual indicators as described above.

Again with respect to FIG. 4, the configuration of the proximal set and distal extension set 220 can vary. In some implementations, the drive fluid can be contained in a drive fluid reservoir 230, such as a drip chamber to spike into a solution container. A clamp, such as a roller clamp or other device, can be used to control flow during priming. The pumping element 232 can include a segment of elastomeric tubing with low compression set characteristics for fluid delivery accuracy. A flow stop device can be used to prevent the free-flow of infusate. Tubing 210 can couple to the hydraulic assembly 215 at proximal inlet 285 having a luer 287 or other device connected with the inlet 285. The hydraulic assembly 215 can couple to the extension set 220 at distal outlet 255 having a luer 295 or other device connected with the outlet 255. A stopcock 294 can be attached to the luer 295 on the outlet 255. The stopcock 294 can allow, for example, a pharmacist to fill the infusate chamber 245 with the medical fluid. The stopcock 294 can also serve as an access port for priming or flushing the extension set 220 or for a secondary medication access. Further, a valve 296, such as an anti-siphon valve, can be attached to the stopcock 294 to prevent accidental siphoning. For example, the valve 296 can protect against fluid being siphoned owing to any hydrostatic pressure differential. The hydraulic assembly 215 can be positioned at patient level to reduce the risk of siphoning. The extension set 220 can provide a relatively short connection to the patient access site.

The hydraulic assembly 215 can include a flexible, dual-chambered reservoir 218 that may or may not be enclosed by a rigid, fixed volume housing 247 as will be discussed in more detail below. The dual-chambered reservoir 218 provides a closed system isolating medical fluids on the infusate side of the system 200 from the components of the drive side of the system 200, such as tubing materials that may be permeable to water vapor or that may leach into the infusate. Isolating the drive side from the infusate side allows for the optimization of one or more of the components of the drive assembly 205. For example, for large volume delivery pumps, silicone tubing, which can be permeable to air can be replaced with an alternate material such as butyl rubber which has a low permeability thereby reducing the incidence of air-in-line alarms. In some implementations, the dual-chambered reservoir 218 can accommodate medication volumes that are relatively large, for example, larger than the volumes accommodated by a syringe barrel. The dual-chambered reservoir 218 can contain 50 mL, 100 mL, 150 mL, 200 mL, 250 mL, 500 mL, 750 mL, 1000 mL or higher. In other implementations, the dual-chambered reservoir 218 can accommodate medication volumes that are smaller, for example, 0.2 mL, 0.25 mL, 0.3 mL, 0.35 mL, 0.4 mL, 0.5 mL, 1.0 mL, 2.0 mL, 2.5 mL, 5.0 mL, 10 mL, 20 mL, 30 mL, or higher. The dual-chambered reservoir 218 also can allow for the mechanical pumping of a driving fluid and the infusate side of the system to be moved much closer to the patient, thereby reducing priming volume lost in the line.

Figure 5A:
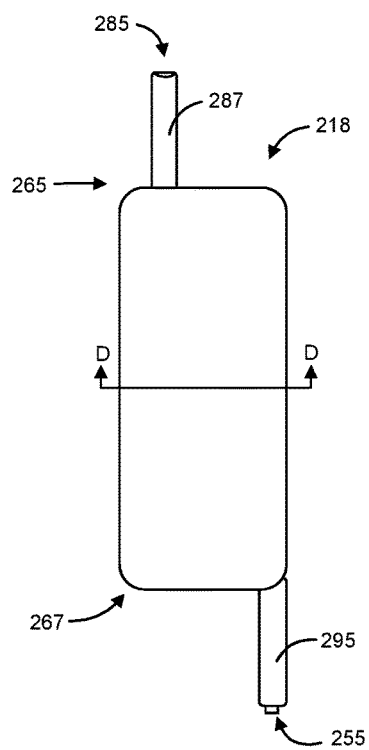
FIG. 5A is a schematic side view of an infusate reservoir according the implementation of FIG. 4.
Figure 5B:
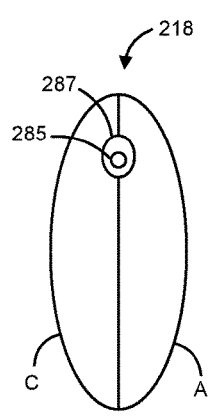
FIGS. 5B and 5C are schematic top and bottom views, respectively, of the infusate reservoir of FIG. 5A.
Figure 5C:
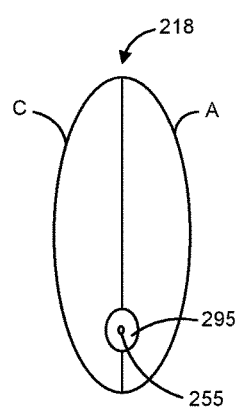
Figure 5D:
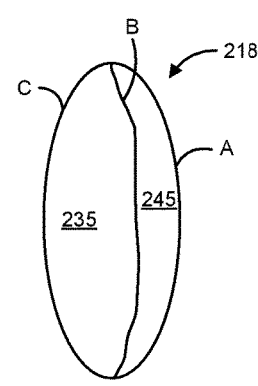
FIG. 5D is a schematic cross-sectional view of the infusate reservoir of FIG. 5A taken along line D-D.

Now with respect to FIGS. 5A-5D and FIGS. 6A-6D, the dual-chambered reservoir 218 can be formed using a tri-layer bag design. The layers can be heat sealed or RF (radiofrequency) sealed with a luer 287, such as a female luer, sealed between one pair of layers, such as layers A and B, at a proximal end 265 forming an inlet 285 to the dual-chambered reservoir 218 as shown in FIGS. 5B and 5D. The layers can also be sealed with a luer 295, such as a male luer, sealed between a second pair of layers, such as layers B and C, on the opposite, distal end 267 forming an outlet 255 from the dual-chambered reservoir 218 as shown in FIGS. 5C and 5D. It should be appreciated that the position of the luers 287, 295 can vary. The perimeter sealing of the A and B layers can form the drive chamber 235 for receiving the drive fluid from the proximal drive set through inlet 285. The perimeter sealing of the B and C layers can form the infusate chamber 245 that contains the infusate. The flexible divider 240 (shown in FIG. 5D as layer B) can divide the drive chamber 235 from the infusate chamber 245 and also aid in the delivery of infusate out of the infusate chamber 245 as will be described below. The layers of the dual-chambered reservoir 218 can be formed of a relatively flexible material including, but not limited to polymeric materials, polyvinyl chloride (PVC), non-DEHP plasticized PVC, ethylene vinyl acetate, polypropylene, copolyester ether, styrene ethylene butadiene and blends of polymer materials. It should be appreciated that one or more of the layers can be the same material or different material. In other implementations, the divider 240 can be a flexible, movable material and the outer layers of the dual-chambered reservoir 218 can be formed of a less flexible, more rigid material. For example, layer B (i.e. the divider 240) can be a flexible material and layers A and C can be formed of a less flexible material. As will be described in more detail below, the less flexible outer layers can limit the volume of the fluid chambers acting as an integrated, fixed-volume housing.

Figure 6A:
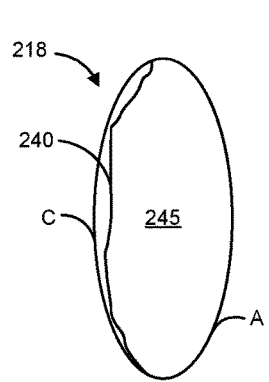
FIGS. 6A-6D are schematic cross-sectional views of the infusate reservoir of FIG. 5A in various stages of infusate delivery.
Figure 6B:
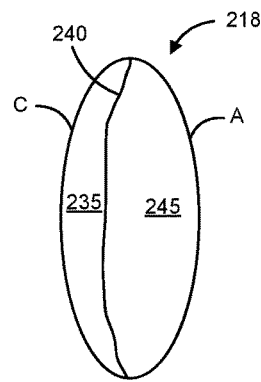
Figure 6C:
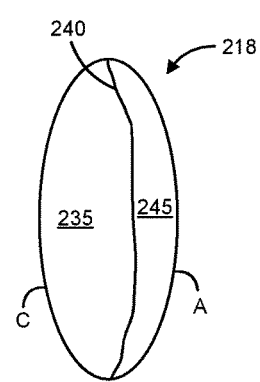
Figure 6D:
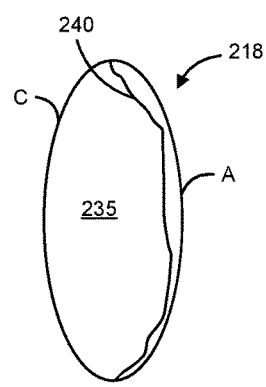

The divider 240 can be a flexible, moveable central element of the reservoir 218 dividing it into two fluid chambers. FIG. 6A illustrates a schematic cross-sectional view of a dual-chambered reservoir 218 having an infusate chamber 245 nearly filled with infusate and a drive chamber 235 that is nearly empty. As the drive chamber 235 fills with fluid through inlet 285 and pressure increases on the drive chamber 235 side of the reservoir 218, the divider 240 is urged away from layer C towards the center of reservoir 218 and towards layer A (see FIGS. 6B and 6C). As this happens, infusate contained in the infusate chamber 245 can exit the infusate chamber 245 through outlet 255 (shown in FIG. 5A). FIG. 6D illustrates the dual-chambered reservoir 218 having an infusate chamber 245 that is nearly empty and a drive chamber 235 nearly full indicating a near end of the infusion.

Figure 7A:
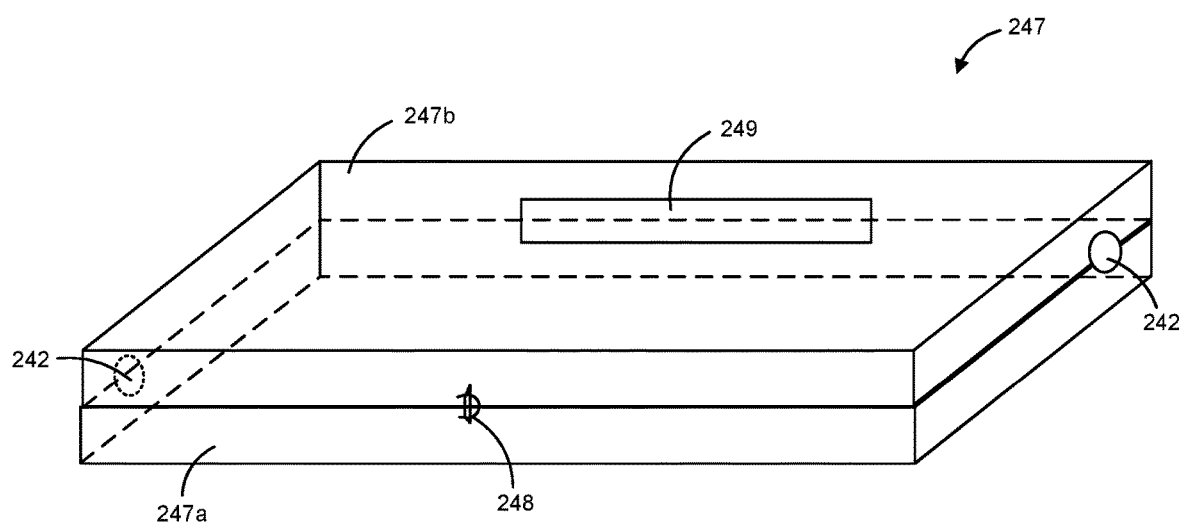
FIGS. 7A-7B are schematic views of a case for housing the infusate reservoir of FIG. 5A.
Figure 7B:
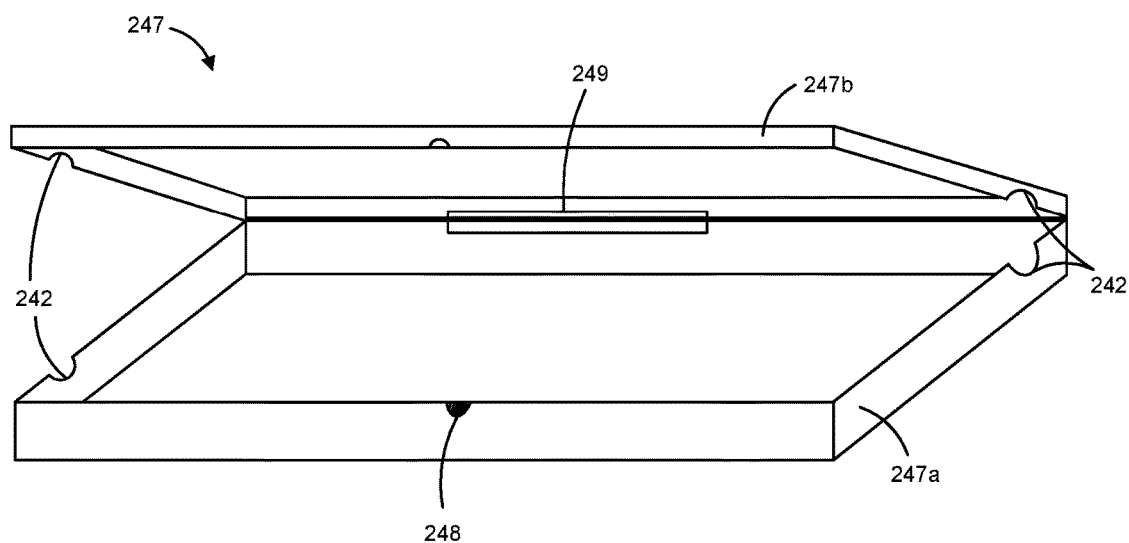

Now turning to FIGS. 7A-7B, the hydraulic assembly 215 also can include an outer housing 247 that is rigid in order to maintain a constant volume in the flexible dual-chambered reservoir 218. The housing 247 can have a volume that is substantially identical to the volume of the dual-chambered reservoir 218 when one of the drive chamber 235 or the infusate chamber 245 is filled to its maximum volume. The housing 247 can be configured to contain one or more reservoirs 218 having a volume of 50 mL, 100 mL, 150 mL, 200 mL, 250 mL, 500 mL, 750 mL, 1000 mL or higher volume. The housing 247 can also be configured to contain one or more reservoirs 218 having a volume of 0.2 mL, 0.25 mL, 0.3 mL, 0.35 mL, 0.4 mL, 0.5 mL, 1.0 mL, 2.0 mL, 2.5 mL, 5.0 mL, 10 mL, 20 mL, 30 mL, or higher volume. The housing 247 can maintain the constant volume in the reservoir 218 so that the amount of drive fluid pumped into the drive chamber 235 assures that displacement of an equal amount of infusate in the infusate chamber 245 through the outlet 255. In some implementations, the housing 247 is formed of clear, rigid material including polystyrene, polyvinyl chloride (PVC), polycarbonate, PET, polyamide (PA), acrylic, epoxy, polyester, or acrylonitrile butadiene styrene (ABS). The housing 247 can include halves 247a, 247b coupled together by one or more hinge elements 249 and a closure mechanism 248 such that the dual-chambered reservoir 218 can be removed and replaced from the housing 247. The housing 247 can include one or more relief sections to accommodate access ports. For example, the housing 247 can include a pair of half-circular relief sections 242 on a proximal end that when mated accommodate the proximal luer 287 at the inlet 285 and a pair of half-circular relief sections 242 on a distal end that when mated accommodate the distal luer 295 at the outlet 255. It should be appreciated the number and shape of the relief sections 242 can be varied. Further, it should be appreciated that the geometry of the housing 247 can vary and is not limited to rectangular as shown in the figures. In other implementations, the outer layers of the dual-chambered reservoir 218 can be formed of a less flexible material and uses no separate rigid housing 247.

Methods of Use

Described below are methods of use of the infusion systems described herein. In one implementation, a user can prime the infusate side of the system and then the drive fluid side of the system. It should be appreciated that the drive fluid side of the system can be primed prior to the infusate side of the system. With respect to FIGS. 1, 2 and 3, a user can fill the infusate chamber 45 of the syringe assembly 15 with a drug or other fluid infusate to be delivered to a patient. The drug can be any liquid infusate as is appropriate for the treatment desired. In one implementation, the divider 40 can be withdrawn distally, such as by manually pulling backward on the handle 52, to cause a vacuum within the infusate chamber 45 and cause infusate to be pulled in from a larger reservoir or vial through the distal outlet 55 and prime the extension set 20. It should be appreciated that filling and priming can be performed by setting the drive assembly 5 into a reverse mode or using syringe filling equipment such as in a pharmacy. Once the desired volume of infusate is within the infusate chamber 45 and the extension set 20 primed, the user can detach the handle 52 and attach the cap 70 onto the proximal end 65 of the syringe assembly 15.

The clinician can then prime the drive fluid side of the system. A first end of the tubing 10 can be attached to the access port 85 of the cap 70 such as via a male luer and a second end of the tubing 10 can be attached to the drive assembly 5. The user can prime the tubing 10 with drive fluid, such as water, contained within the drive fluid reservoir 30 of the drive assembly 5. The drive assembly 5 can drive fluid from the drive fluid reservoir 30 in a first direction through tubing 10 to cause the divider 40 to move distally due to increased fluid pressure within drive chamber 35. As the divider 40 moves distally through the housing 47, infusate contained within the infusate chamber 45 is expelled through the distal outlet 55 into extension set 20 towards the patient access site 25.

The drive assembly 5 can be driven in a reverse direction to re-prime the infusate side of the system 100. The syringe assembly 15 can include a stopcock 94 having a one-way valve for refill of the infusate chamber 45. During refill of the infusate chamber 45, the user can attach a separate syringe or other container having a supply of infusate to the open port of the stopcock 94 and turn the handle on the stopcock 94 to allow flow between the infusate chamber 45 and the infusate-filled syringe. The handle can then be turned off to the patient's access site 25. The one-way valve at the patient side of the stopcock 94 can prevent accidental drawback from the patient.

In another implementation and with respect to FIG. 4, a user can prime the infusate side of the system 200 and then the drive fluid side of the system 200. A user, such as a pharmacist, can fill the infusate chamber 245 with a drug or other fluid infusate to be delivered to a patient. The drug can be any liquid infusate as is appropriate for the treatment desired. In one implementation, a syringe or other system can be used to inject a fluid into the outlet 255 to load the infusate chamber 245. The stopcock 294 having a one-way valve 296 can be used for fill and/or refill of the infusate chamber 245. During filling of the infusate chamber 245, the user can attach a separate syringe or other container having a supply of infusate to the open port of the stopcock 294 and turn the handle on the stopcock 294 to allow flow between the infusate chamber 245 and the infusate-filled syringe. Once the desired volume of infusate is within the infusate chamber 245 and the extension set 220 primed, the user can enclose the reservoir 218 in the housing 247.

The clinician can prime the drive fluid side of the system 200. A first end of the tubing 210 can be attached to the access port 285 of the reservoir 218 available through the relief sections 242 of the housing 247 and a second end of the tubing 210 can be attached to the pumping element 232. The user can prime the tubing 210 with drive fluid, such as water, contained within the drive fluid reservoir 230 of the drive assembly 205. The pumping element 232 can drive fluid from the drive fluid reservoir 230 in a first direction through tubing 210 to cause the divider 240 separating drive fluid chamber 235 from infusate chamber 245 to move due to increased filling of and increased fluid pressure within drive chamber 235. As the divider 240 moves within the reservoir 218, infusate contained within the infusate chamber 245 is expelled through the distal outlet 255 into extension set 220 towards the patient 225.

As used herein, "proximal" or "upstream" generally means closer to the user or a part of the system that is located closer to the user and further away from the patient in the sense of fluid flow through the system. As used herein, "distal" or "downstream" generally means closer to the patient or a part of the system that is located closer to the patient and further away from the user in the sense of fluid flow through the system. Similarly, as used herein "drive fluid side" generally refers to a part of the infusion system that is in fluid communication with the drive assembly 5, 205; drive chamber 35, 235; and/or tubing 10, 210. The phrase "infusate fluid side" generally refers to a part of the infusion system that is in fluid communication with the infusate chamber 45, 245; extension set 20, 220; and/or the patient access site 25; 225. It should be appreciated that "drive fluid" can be a fluid including a liquid or gas.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

What is claimed is:

1. An infusion system, comprising:
 a drive assembly comprising:
  a drive fluid reservoir; and
  a drive mechanism configured to apply a force to drive fluid from the drive fluid reservoir through a length of tubing; and
 a hydraulic assembly comprising a syringe assembly having a syringe barrel:
  a first fluid chamber having an inlet port configured to be in fluid communication with the drive fluid reservoir through the length of tubing;

a second fluid chamber having an outlet port configured to be in fluid communication with a patient extension set;
a cap coupled to and sealing off a proximal end of the first fluid chamber;
a flexible movable divider positioned within the syringe barrel and sealing the first fluid chamber from the second fluid chamber; and
a plunger having a detachable handle and being movable relative to the divider within the syringe barrel;
wherein the force applied by the drive mechanism propels the fluid from the drive fluid reservoir through the length of tubing into the first fluid chamber to move the divider causing infusate to exit the second fluid chamber through the outlet port.

2. The system of claim 1, wherein the cap comprises a stem portion configured to extend within and seal with an inner surface of the first fluid chamber.

3. The system of claim 1, wherein the inlet port extends through the cap.

4. The system of claim 1, wherein the cap further comprises a vent filter.

5. The system of claim 1, wherein the drive assembly further comprises one or more pressure sensors.

6. The system of claim 1, wherein the drive assembly further comprises one or more visual indicators providing information regarding operation of the system.

7. The system of claim 6, wherein the one or more visual indicators comprise one or more LEDs illuminating one or more components of the system.

8. The system of claim 7, wherein a color of the one or more LEDs indicates infusion status.

9. The system of claim 1, wherein the length of tubing is low-compliance tubing.

10. The system of claim 1, wherein the hydraulic assembly is reversibly coupled to the drive assembly.

11. The system of claim 1, wherein the patient extension set is less than 6 inches.

12. The system of claim 1, wherein the patient extension set has a priming volume of less than about 0.7 mL.

13. An infusion system, comprising:
a drive assembly comprising:
a drive fluid reservoir; and
a drive mechanism configured to apply a force to drive fluid from the drive fluid reservoir through a length of tubing; and
a hydraulic assembly comprising a syringe assembly having a syringe barrel:
a first fluid chamber having an inlet port configured to be in fluid communication with the drive fluid reservoir through the length of tubing;
a second fluid chamber having an outlet port configured to be in fluid communication with a patient extension set;
a flexible movable divider positioned within the syringe barrel and sealing the first fluid chamber from the second fluid chamber; and
a cap coupled to and sealing off a proximal end of the first fluid chamber;
wherein the force applied by the drive mechanism propels the fluid from the drive fluid reservoir through the length of tubing into the first fluid chamber to move the divider causing infusate to exit the second fluid chamber through the outlet port.

14. The system of claim 13, further comprising a plunger reversibly coupled to the divider and having a detachable handle.

15. The system of claim 13, wherein the cap comprises a stem portion configured to extend within and seal with an inner surface of the first fluid chamber.

16. The system of claim 13, wherein the inlet port extends through the cap.

17. The system of claim 13, wherein the cap further comprises a vent filter.

18. The system of claim 13, wherein the drive assembly further comprises one or more pressure sensors.

19. The system of claim 13, wherein the drive assembly further comprises one or more visual indicators providing information regarding operation of the system.

20. The system of claim 19, wherein the one or more visual indicators comprise one or more LEDs illuminating one or more components of the system.

21. The system of claim 20, wherein a color of the one or more LEDs indicates infusion status.

22. The system of claim 13, wherein the length of tubing is low-compliance tubing.

23. The system of claim 13, wherein the hydraulic assembly is reversibly coupled to the drive assembly.

24. The system of claim 13, wherein the patient extension set is less than 6 inches.

25. The system of claim 13, wherein the patient extension set has a priming volume of less than about 0.7 mL.

* * * * *